United States Patent
Boschung, Jr. et al.

(10) Patent No.: US 6,511,220 B1
(45) Date of Patent: Jan. 28, 2003

(54) METHOD AND DEVICE FOR GENERATING A SIGNAL ACCORDING TO A LIQUID FILM ON A SURFACE

(75) Inventors: Marcel Boschung, Jr., Neyruz; Etienne Bornand, Autigny, both of (CH)

(73) Assignee: Boschung Mecatronic AG, Granges-Paccot (CH)

( * ) Notice: Subject to any disclaimer, the term of this patent is extended or adjusted under 35 U.S.C. 154(b) by 0 days.

(21) Appl. No.: 09/486,720

(22) PCT Filed: Sep. 9, 1998

(86) PCT No.: PCT/IB98/01396
§ 371 (c)(1),
(2), (4) Date: Apr. 11, 2000

(87) PCT Pub. No.: WO99/13295
PCT Pub. Date: Mar. 18, 1999

(30) Foreign Application Priority Data

Sep. 9, 1997 (EP) .............................. 97115582

(51) Int. Cl.⁷ ............................ G01N 25/00; G01K 1/08
(52) U.S. Cl. ........................................ 374/7; 374/142
(58) Field of Search .................... 374/7, 16, 102, 374/142, 164, 165; 33/521

(56) References Cited

U.S. PATENT DOCUMENTS

| | | | |
|---|---|---|---|
| 2,972,882 A | * 2/1961 | Erwin | 374/7 |
| 3,413,474 A | * 11/1968 | Freeh | 374/7 |
| 3,434,347 A | 3/1969 | Lockwood | |
| 3,535,522 A | * 10/1970 | Green | 374/7 |
| 3,869,984 A | * 3/1975 | Toth | 73/150 R |
| 3,973,122 A | * 8/1976 | Goldberg | 374/7 |
| 4,513,384 A | * 4/1985 | Rosencwaig | 374/7 |
| 4,687,333 A | 8/1987 | Odasima et al. | |
| 4,842,410 A | * 6/1989 | Darrah et al. | 356/505 |
| 4,897,597 A | 1/1990 | Whitener | |
| 5,218,206 A | 6/1993 | Schmitt et al. | |
| 5,258,824 A | * 11/1993 | Carlson et al. | 374/7 |
| 5,418,522 A | 5/1995 | Freundlieb et al. | |
| 5,433,106 A | 7/1995 | Matsumura et al. | |
| 5,590,560 A | * 1/1997 | Joos et al. | 73/64.48 |
| 5,714,691 A | * 2/1998 | Hill | 73/861.04 |
| 6,128,081 A | * 10/2000 | White et al. | 356/432 |

FOREIGN PATENT DOCUMENTS

| | | |
|---|---|---|
| CA | 1163461 | 3/1984 |
| DE | 3118997 | 1/1983 |
| EP | 0045106 | 2/1982 |
| EP | 362173 | 4/1990 |
| EP | 432360 | 6/1991 |
| EP | 0762359 | 3/1997 |
| GB | 1364845 | 4/1974 |
| GB | 1434605 | 5/1976 |
| GB | 2056057 | 3/1981 |

OTHER PUBLICATIONS

Patent Abstracts of Japan, vol. 97, No. 8, published Aug. 29, 1997 of JP 09089546.
Patent Abstract of Japan 03–024449 published Feb. 1, 1991.
Patent Abstract of Japan 03–082944 published Apr. 8, 1991.

* cited by examiner

*Primary Examiner*—Diego Gutierrez
*Assistant Examiner*—Yaritza Guadalupe
(74) *Attorney, Agent, or Firm*—Greenblum & Bernstein, P.L.C.

(57) ABSTRACT

Device and a process for generating a signal dependent upon a liquid film on a surface. The device includes one of a heating arrangement and a cooling arrangement for subjecting a portion of the liquid film to a temperature change, a temperature measuring arrangement for determining the temperature of the liquid film, the temperature measurement arrangement being capable of producing a signal, and a control and evaluation device for controlling one of the heating arrangement and the cooling arrangement and the temperature measuring arrangement. The process includes subjecting a portion of the liquid film to a temperature change using one of a heating and a cooling arrangement, measuring a temperature of the portion using a temperature measuring arrangement, assigning a value which corresponds to a thickness of the liquid film to the temperature change using an evaluation device, and producing a signal.

26 Claims, 3 Drawing Sheets

METHOD AND DEVICE FOR GENERATING A SIGNAL ACCORDING TO A LIQUID FILM ON A SURFACE

CROSS-REFERENCE TO RELATED APPLICATIONS

The present application is a U.S. National Stage Application of International Application No. PCT/IB98/01396, filed on Sep. 2, 1998, and claims priority under 35 U.S.C. §119 of European Application No. 97115582.5, filed on Sep. 9, 1997.

BACKGROUND OF THE INVENTION

1. Field of the Invention

The invention relates to a process for generating a signal dependent upon a liquid film on a surface, particularly a traffic surface. The invention furthermore relates to a device for generating a signal dependent upon a liquid film on a surface, particularly a traffic surface, and the use of such a process or device in an arrangement for determining the freezing point of the liquid.

2. Description of Background and Relevant Information

It is desirable to produce a signal that provides information on the thickness of a liquid film on traffic surfaces, which are understood as roads and rolling and starting/landing runways for aircraft, for example. Information can be obtained thereby on the danger of so-called hydroplaning (the floating of vehicle wheels on the portion of the water film impenetrable to the wheels), or a warning can be transmitted to users of the traffic surface. As is known, the danger of hydroplaning increases with the increasing thickness of the water film. Measuring the thickness of the water film as precisely as possible by way of the reflection of micro-waves is known from EP-A-0 432 360. But the process is an elaborate one. From U.S. Pat. No. 4,897,597, it is known that the water film thickness can be ascertained by measuring conductivity which, however, does not always lead to satisfactory results. DE-A-31 18 997, EP-A-0 045 106, and EP-A-362 173 disclose processes for determining the freezing point of a liquid but not for ascertaining the water film thickness. Patent Abstracts of Japan vol. 97, no. 8, Aug. 29, 1997 discloses the detection of an ice film thickness, where the thickness is detected by way of the installation distance of a temperature sensor from a heat exchanger line that is icing up.

SUMMARY OF THE INVENTION

The invention therefore provides for a simple and economical process for generating a signal that is dependent upon the liquid film. The invention is also directed to a corresponding device.

It has been shown that, by heating or cooling a portion of the liquid film and by measuring the increase or decrease in temperature with sufficient accuracy, a conclusion can be reached at least on the thickness range in which the liquid film thickness lies. As a rule, assigning the liquid film thickness to a thickness range or class suffices for the purposes of a hydroplaning warning. The process also permits the absolute thickness to be determined with a good degree of accuracy if a greater degree of effort is taken in evaluating the temperature curve.

The preferred device is one with a Peltier element for heating the liquid film. The reverse operation of the Peltier element also permits a cooling of the liquid film. Thus, the device can be additionally used to determine the freezing point of the liquid according to the process indicated in EP-A-0 045 106 or EP-A-0 362 173.

The invention provides for a process for generating a signal dependent upon a liquid film on a surface, particularly a traffic surface, characterized in that a portion of the liquid of the liquid film is heated or cooled by a heating arrangement or a cooling arrangement, the increase or decrease in the temperature of the heated or cooled portion is ascertained by a temperature measuring arrangement, and a value or value range for the thickness of the liquid film is assigned to the temperature increase or decrease by an evaluation device and is released as a signal. The process may be characterized in that an area is provided in the heating arrangement or cooling arrangement which is indented relative to the surface and in which area the liquid is heated. The process may be characterized in that the heating output or cooling output is kept constant during heating or cooling. The process may be characterized in that the initial temperature $T_0$ of the liquid film is determined in each case before or at the beginning of heating or cooling. The process may be characterized in that a test on the presence of liquid is performed before the beginning of heating or cooling, and the heating arrangement or cooling arrangement is only activated when liquid is identified.

The invention also provide for a device for generating a signal dependent upon a liquid film on a surface, particularly a traffic surface, characterized in that a heating arrangement or a cooling arrangement by way of which a portion of the liquid film can be heated or cooled is provided, as well as a temperature measuring arrangement for determining the temperature of the liquid film that can be heated or cooled by the heating arrangement or cooling arrangement, and a control and evaluation device by way of which the heating arrangement or the cooling arrangement and the temperature measuring arrangement can be controlled and the signals of the temperature measuring arrangement can be evaluated, specifically in such a way that a thickness, or thickness range, of the liquid film is assigned to the measured temperature increase or decrease and is released as a signal. The device may be characterized in that said device includes mechanisms, particularly an electrode arrangement, for identifying the presence of liquid in the area of the heating arrangement. The device may be characterized in that the heating arrangement or cooling arrangement includes at least one Peltier element which is operated at a constant power. The device may be characterized in that said device exhibits a surface which can be aligned so as to be flush with the area, such that the liquid film uniformly covers the area and the surface of the device, and in the area of the heating arrangement or the cooling arrangement an indentation is provided in the surface.

The invention also provides for using the process in an arrangement for generating a signal indicating the freezing point of the liquid on the surface.

According to another aspect of the invention, there is provided a process for generating a signal dependent upon a liquid film on a surface, comprising subjecting a portion of the liquid film to a temperature change using one of a heating and a cooling arrangement, measuring a temperature change of the portion using a temperature measuring arrangement, assigning a value to the temperature change using an evaluation device which is related to a thickness of the liquid film, and producing a signal related to the value. The surface may be one of a road surface and a traffic surface. The assigning a value may comprise assigning a value range. The temperature change may comprise one of a temperature increase and a temperature decrease. The heating or cooling arrangement may comprise one of a heating and a cooling surface which is indented some distance from another surface of the arrangement. The liquid may be one of heated and cooled in the indented heating and cooling surface. The subjecting may comprise producing one of a constant heating output and a constant cooling output. One of the heating and the cooling arrangement may be adapted to produce one of a constant heating output and a constant cooling output.

The process may further comprise determining an initial temperature $T_0$ of the liquid film. The determining may occur either before or at a beginning of the subjecting. The process may further comprise testing for the presence of the liquid film. The testing may be performed before the subjecting. The process may further comprise activating the heating or cooling arrangement upon identifying the presence of the liquid film.

The invention provides for a device for generating a signal dependent upon a liquid film on a surface comprising one of a heating arrangement and a cooling arrangement for subjecting a portion of the liquid film to a temperature change, a temperature measuring arrangement for determining the temperature of the liquid film, the temperature measurement arrangement being capable of producing a signal, and a control and evaluation device for controlling one of the heating arrangement and the cooling arrangement and the temperature measuring arrangement. The device may generate the signal when one of a predetermined thickness and a predetermined thickness range of the liquid film is ascertained. The surface may be one of a road surface and a traffic surface. The device may further comprise an electrode arrangement for identifying the presence of the liquid film in an area of the heating or cooling arrangement. The temperature measurement arrangement may comprise a measurement device which is connected to the electrode arrangement. The heating or cooling arrangement may comprise at least one Peltier element which is operated at a constant power. The heating or cooling arrangement may comprise one of a heating and a cooling surface which is indented some distance from an exterior surface of the arrangement. The liquid may be one of heated and cooled in the indented heating and cooling surface. The exterior surface may be adapted to be aligned with a road surface when the device is disposed in the road surface.

The invention also provides for a method for generating a signal dependent upon a liquid film on a surface with a device that includes one of a heating arrangement and a cooling arrangement for subjecting a portion of the liquid film to a temperature change, a temperature measuring arrangement for determining the temperature of the liquid film, the temperature measurement arrangement being capable of producing a signal, and a control and evaluation device for controlling one of the heating arrangement and the cooling arrangement and the temperature measuring arrangement, the method comprising subjecting the portion of the liquid film to a temperature change using one of the heating and the cooling arrangement, measuring the temperature of the portion using the temperature measuring arrangement, assigning the value which corresponds to the thickness of the liquid film to the temperature change using the evaluation device, and producing a signal related to the value.

BRIEF DESCRIPTION OF THE DRAWINGS

In the following, embodiment examples of the process and device are explained in greater detail on the basis of the drawings.

DETAILED DESCRIPTION OF THE INVENTION

Figure 1:
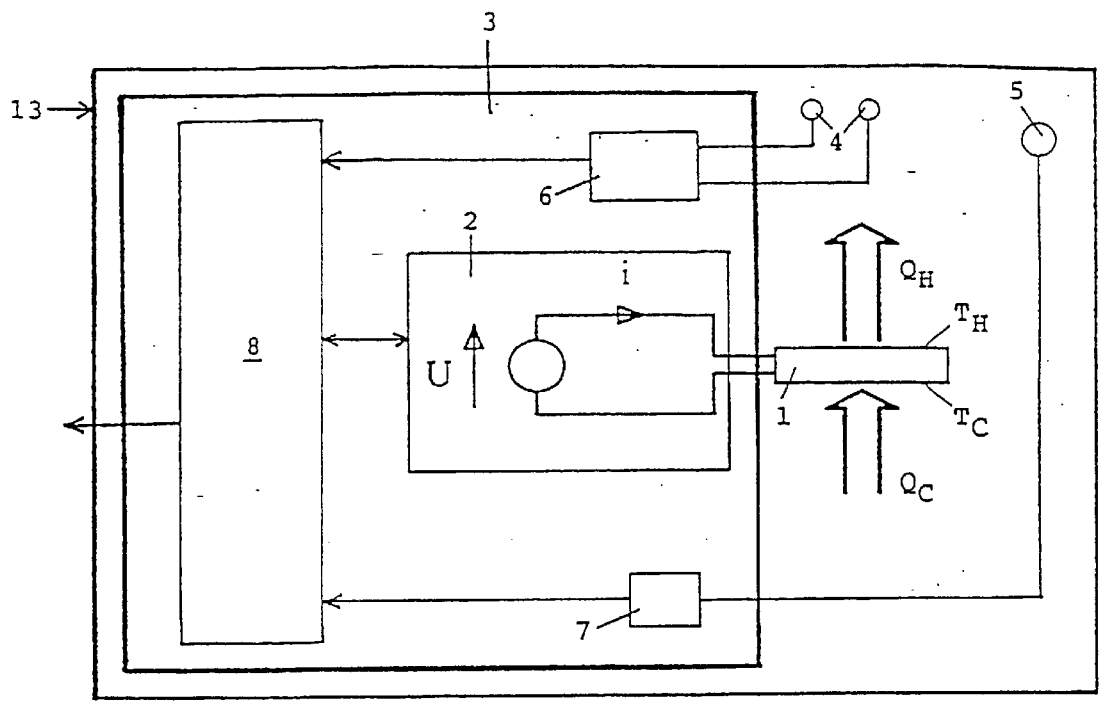
FIG. 1 schematically depicts the electrical design of a device for implementing the process.
Figure 2:
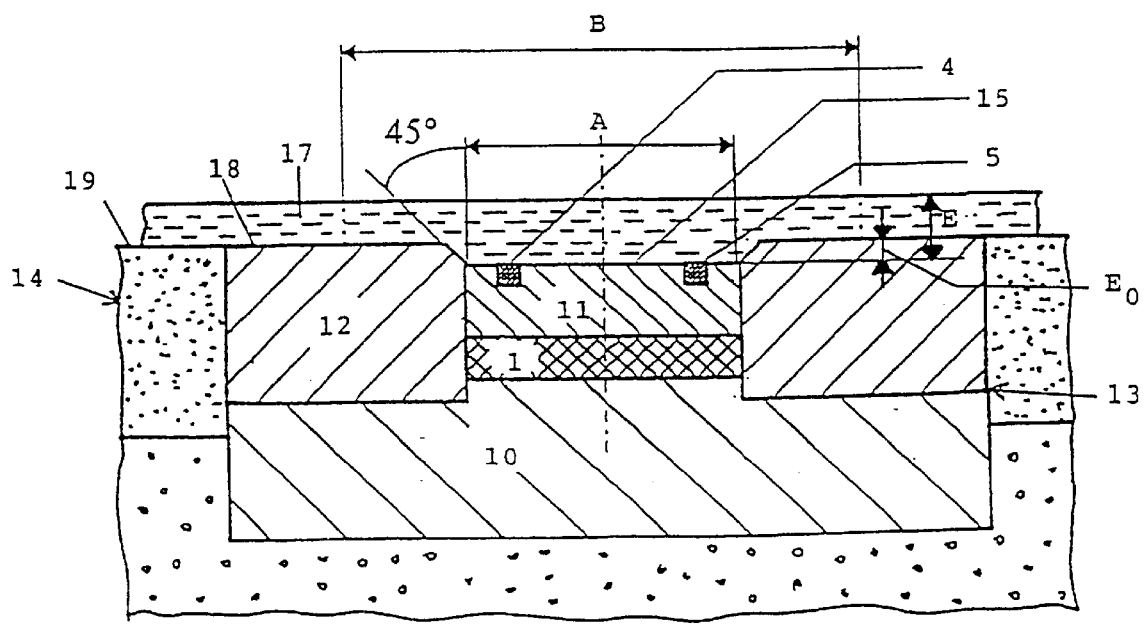
FIG. 2 schematically depicts the structural design of a device for implementing the process.

FIGS. 1 and 2 show in a simplified, schematic form the electrical and structural design of a device according to the invention. Here, a Peltier element is used to heat the liquid film. This is to be understood merely as an example, since basically the liquid film can be heated with any desired heating source, e.g., with an electrical resistance heating unit. As already mentioned, cooling can occur instead of heating, but heating will be taken as an example in the discussion below. In FIG. 1 the Peltier element 1 is depicted schematically as a block. Electrical power comes from a feed circuit 2 which, in the present example, is located inside a control and evaluation circuit 3. The feed circuit 2 includes an electrical source, which can be, e.g., a constant current source with a constant current i, or a source with a non-constant or known current progression. The heat $Q_H$, which is produced on the warm side of the Peltier element, is given by the formula $Q_H = Q_C + U \cdot i$, where $Q_C$ is the heat removed from the cold side of the Peltier element and U and i indicate the voltage, or the current, at the Peltier element. $T_C$ and $T_H$ are the temperatures of the cold and warm sides of the Peltier element. With a reversed direction of flow, the Peltier element can also be used for cooling, since the cold and hot side are then exchanged.

FIG. 2 shows the Peltier element 1 secured between a heat-conducting body 10, e.g., of copper, and a second heat-conducting body 11, e.g., of aluminum. Together with the housing block 12, made of a material that is a poor heat conductor, the elements 1, 10, and 11 form the device 13, which can be embedded in the form of a ground probe beneath the surface on which the water film will rest. In the depicted example, a road 14 with different layers is schematically suggested; the probe is installed in this road in such a way that the surface 18 of the probe 13 lies level with the surface 19 of the road 14. The body 10 of the probe is embedded in the earth, or in the roadbed, so as to withdraw heat from this earth or roadbed, while the heat is used to heat the water film 17. With its surface 15, the heat-conducting body 11 positioned above the Peltier element 1 forms the heating surface for the water film. Further electrodes 4 can be provided in the probe 13, so that which a conductivity measurement can be performed to determine whether a water film is present or not. To this end, the electrodes 4 are connected to a corresponding measuring device 6, which in turn is attached to a control and evaluation element 8, specifically a microprocessor, belonging to the control and evaluation device 3. Such electrodes can also be provided in place of the probe at a different place on the road. Furthermore, a temperature-measuring resistor 5, also in contact with the water film, is positioned in the probe, so that which the temperature of the liquid film can be measured.

This measuring resistor, usually a known Pt100 element or also a thermoelement, is also connected to the microprocessor 8 by way of a corresponding measurement circuit 7. The temperature can also be measured by the Peltier element, as known from EP-A-0 362 173.

Naturally, the indicated design and installation of the probe 13 are to be understood only as an example. As mentioned, the probe can include a different kind of heating element and can be positioned in a different manner, next to or above the surface upon which the water film is to be measured; care must be taken to position the surface of the probe in such a way that a water film usually forms on it that is identical to the one on the surface to be observed. Also, the evaluation and control device can naturally have a different design than that shown in the example, e.g., one consisting of separate elements. As already stated, the electrodes 4 also do not have to be positioned in the probe.

Figure 3:
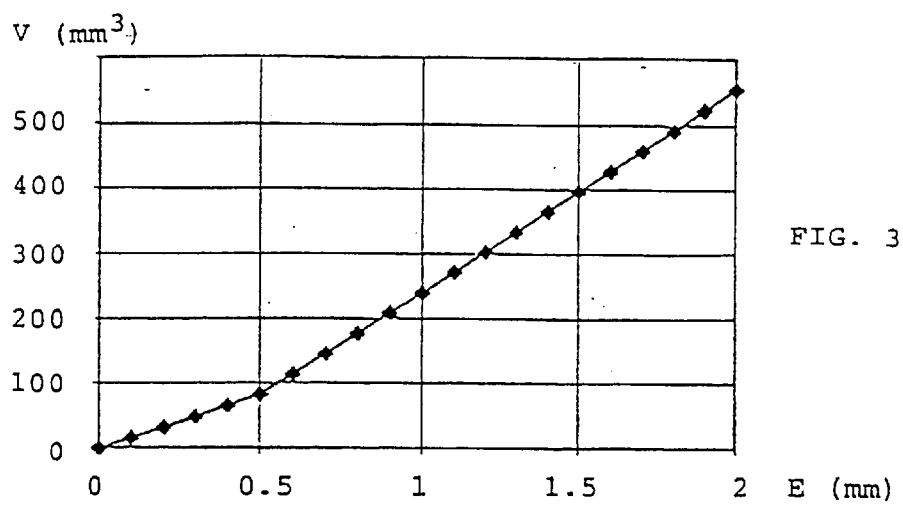
FIG. 3 shows in approximate fashion the dependence of the heated liquid volume on the thickness of the liquid film for the device according to FIG. 2.

In the example shown, the surface 18 of the probe exhibits an indentation which is formed by the surface 15 of the body 11 and which forms a circular area with a diameter A in the example shown. The transitional zone from this area 15 to the level surface 18 of the probe 13 is beveled at an angle of 45°. In heating the water film 17 with the heating arrangement, it can be assumed in a rough approximation that the water film is heated in a circular area of a diameter B. The indentation of the surface of the probe 13 can have, e.g., a depth $E_0$ of 0.5 mm. The diameter A can equal 14 mm and the diameter B can equal 20 mm. The indentation results in a non-linear dependency of the water film volume V on the thickness of the water film E, as shown schematically in FIG. 3. The indentation in the probe is preferred in order to make available a defined quantity of water, even in the case of a very small water film thickness E. Otherwise, there is the danger that, when the water film thickness is very small, the water film will vaporize when heated, which can render a meaningful measurement impossible.

Figure 4:
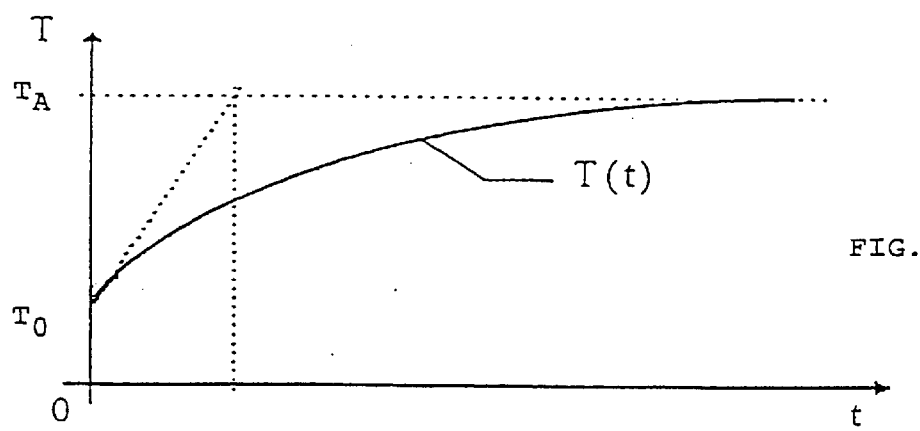
FIG. 4 schematically depicts the increase in temperature of the heated liquid.

To produce a signal that is dependent on the water film and that indicates its thickness, the following procedure is followed. A resistance measurement employing the electrodes, if provided, will preferably ascertain whether there is any water on the measuring probe 13. A very high or infinite resistance value means that the surface of the probe is dry. In this case, heating with the Peltier element is not introduced, and the output signal of the probe 13, or its control and evaluation unit, indicates that a water film is not present. On the other hand, if the resistance measurement yields a finite value signaling the presence of liquid, the heating configuration 1, 10, 11 is activated. The energy to be conducted to the water is determined by the specific heat of water, which equals $4.185 \cdot 10^3$ J kg$^{-1}$ K$^{-1}$. In this case, it is assumed that the water is present in liquid form at the start of heating. If this is not the case, the specific heat of ice and the melting heat must be taken into account. For a known volume, or the resulting thickness of the water film, an initial approximation can assume an exponential temperature curve of temperature T as a function of time, which can be expressed with the equation $$T(t)=T_A-(T_A-T_0)\cdot e^{-t/\tau} \qquad (2)$$

where $T_0$ is the initial temperature, $T_A$ is the asymptotic temperature, and $\tau$ is the time constant for heating. FIG. 4 schematically depicts the corresponding temperature curve. According to one aspect of the invention, the water film thickness is not indicated in a more precise quantitative form, but rather qualitatively by specification of the water film thickness range in which the actual water film thickness lies. For this reason, it is not necessary to perform a precise calculation of the dynamic behavior of the temperature increase in the water film. This could be performed, however, if the water film thickness was to be precisely given. For this calculation, it is necessary to know the thermal conductivity of the water film (temperature gradient), the heat exchange between air and water due to convection, radiation, and water evaporation, the heat losses in the probe, and the behavior of the Peltier element and of the aluminum part 11; it is also necessary to take into account the difference in the thermal behavior between pure water and salt solution.

As a rule, however, it is sufficient for the signal to indicate the water film thickness in such way that the water film thickness can be divided into different classes. This is possible, e.g., with the following table.

| Class | Road Condition | E [mm] |
|---|---|---|
| 1 | dry | 0 |
| 2 | moist | 0 to 0.1 |
| 3 | wet 1 | 0.1 to 0.5 |
| 4 | wet 2 | 0.5 to 1 |
| 5 | wet 3 | >1 |

Five classes are provided here; in class 1 there is dryness; in class 2 the traffic surface is merely moist; in classes 3–5 there are different areas of wet pavement. As a rule, this kind of classification suffices for an effective hydroplaning warning.

FIG. 4 shows the increase in the water film temperature.

Figure 5:
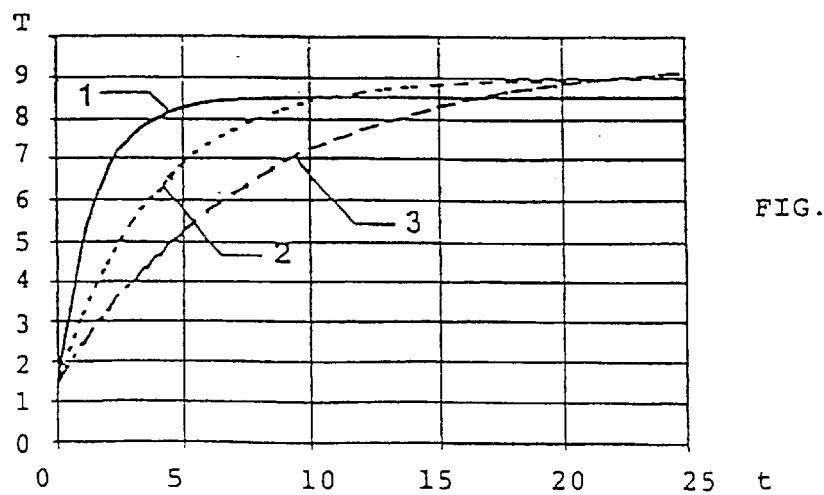
FIG. 5 schematically depicts the increase in temperature for three different thicknesses of the liquid film.
Figure 6:
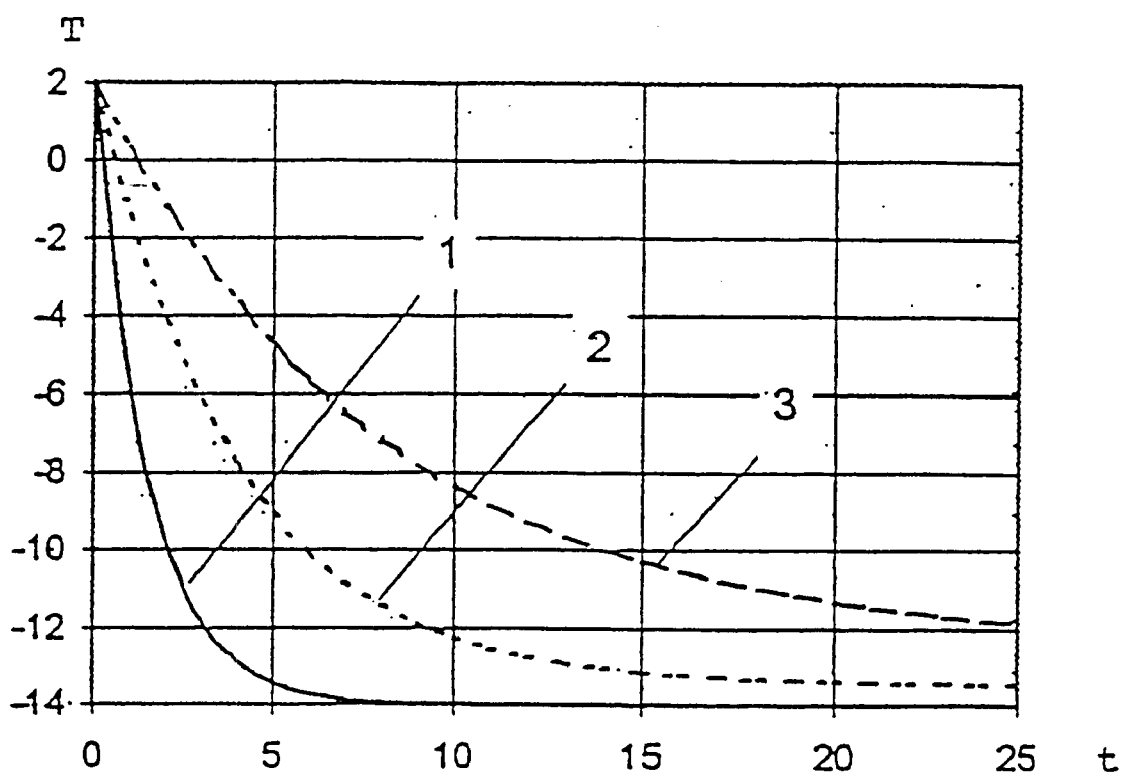
FIG. 6 schematically depicts the decrease in temperature for three different thicknesses of the liquid film.

The increase diminishes progressively, reaching zero when the temperature reaches the asymptotic value $T_A$. At this moment, the system is in dynamic equilibrium, and the released output is equal to the power introduced by the heating configuration. The progression described by the temperature increase is then characteristic for the volume and/or the water film thickness. FIG. 5 shows three examples for different water film thicknesses, where curve 1 represents a slight water film thickness, curve 2 a moderate water film thickness, and curve 3 a large water film thickness. The scale for FIG. 5 is given in arbitrary units for time and temperature and not in seconds and °C. The evaluating device can now determine from the curve which class of water film thickness area the actual water film that produced the given curve during heating should be assigned to. Thus, the water film that produced curve 1 would be assigned to class 2 or 3, independently, of course, of the concrete scale of FIG. 5, which is not indicated, and the water film that produced curve 2 to class 3 or 4, and the water film that produced curve 3 to class 4 or 5. FIG. 6 shows the corresponding curves for cooling of the water film. The curves for temperature increase are naturally not present in graphic form in the evaluation device 3, but rather are available as a succession of stored temperature measuring data from the temperature sensor 5 which are stored in memory belonging to the microprocessor 8. The curve can be depicted by a more or less large number of measured data for temperature. Ideally, the first measured data for temperature $T_0$ is formed before or precisely at the outset of heating and indicates the initial temperature of the water film. Temperature measuring data can be subsequently obtained at different time intervals; naturally, the temperature curve can be more precisely established the more measuring data are stored between $T_0$ and the point at which the asymptotic temperature $T_A$ is reached. To evaluate the stored temperature measuring data, the evaluation device 3 or the microprocessor can employ various, already known processes. First, an approximation of the measured data can be made with function (2), in which values $T_A$ and $\tau$ can be deduced which are in turn a function of the thickness E (for the given volume of the water to be heated, which is determined by the assumed radius B of the heated water area). As an alternative to the approximation method, the increase $\Delta T$ in temperature during a fixed time $T^*$ after the beginning of heating can be measured. $\Delta T^*$ can be expressed as $$\Delta T^* = T(t^*) - T_0 = (T_A - T_0) \cdot (1 - e^{-t^*/\tau}) \tag{3}$$

and the water film thickness can in turn be deduced from this using $T_A$ and $\tau$.

For a precise measurement of the water film thickness, the thickness values $\epsilon$ can be stored in a table, according to a classification of any desired fineness. The applicable tabular value can then be deduced from the evaluation of the curve.

As a further variation, it is possible to measure, starting with the beginning of heating at time t=0, the time $t_x$ which is needed until a predetermined temperature increase $\Delta T_x$ is reached. From equation 2 and the following equations 4 and 5, the water film thickness E in turn can be determined using values $T_A$ and $\tau$.

$$t(T) = \tau \cdot \ln \frac{T_A - T_0}{T_A - T} \tag{4}$$

$$t_x = t(T_0 - \Delta T_x) = \tau \cdot \ln \frac{T_A - T_0}{T_A - T_0 - \Delta T_x} \tag{5}$$

With the evaluation method shown here, it is possible to classify the water film thicknesses into the desired classes and a corresponding signal can be released by the evaluation device.

As already mentioned, a process for determining the freezing point of a liquid is known from EP-A-0 045 106 and EP-A-0 362 173. Such processes can also be implemented with the described probe, so that it is possible to produce both an ice warning and a hydroplaning warning with a single probe in the pavement.

Even if there is ice on the probe, it can first be melted in order to ascertain the water film thickness. The probe can then be cooled in order to determine the freezing point. It is also possible, however, that the melting point will be ascertained during thawing, which will also reveal the freezing point temperature. Separate probes can also be provided, however, in order to determine the water film thickness and the freezing point. In this case, the device for determining the water film thickness will ideally be used in a configuration for determining the freezing point. Knowledge of the water film thickness is useful in ascertaining the freezing point, since from it the concentration of the thawing agent in the liquid can be deduced, given a known quantity of applied thawing agent per surface unit.

What is claimed is:

1. A process for generating a signal dependent upon a liquid film on a surface, comprising:
    subjecting a portion of the liquid film to a temperature change using a temperature changing arrangement which can at least one of heat the liquid film and cool the liquid film;
    measuring a temperature change of the portion using a temperature measuring arrangement;
    assigning a value to the temperature change using an evaluation device, the value being related to a thickness of the liquid film; and
    producing a signal related to the value.

2. The process of claim 1, wherein the surface is one of a road surface and a traffic surface.

3. The process of claim 1, wherein the assigning a value comprises assigning a value range.

4. The process of claim 1, wherein the temperature change comprises one of a temperature increase or a temperature decrease.

5. The process of claim 1, wherein the temperature changing arrangement comprises one of a heating and a cooling surface which is indented some distance from another surface of the arrangement.

6. The process of claim 5, wherein the liquid is one of heated and cooled in the indented heating and cooling surface.

7. The process of claim 1, wherein the subjecting comprises producing one of a constant heating output and a constant cooling output.

8. The process of claim 1, wherein the temperature changing arrangement is adapted to produce at least one of a constant heating output and a constant cooling output.

9. The process of claim 1, further comprising determining an initial temperature $T_0$ of the liquid film.

10. The process of claim 9, wherein the determining occurs either before or at a beginning of the subjecting.

11. The process of claim 1, further comprising testing for the presence of the liquid film.

12. The process of claim 11, wherein the testing is performed before the subjecting.

13. The process of claim 12, further comprising activating the heating or cooling arrangement upon identifying the presence of the liquid film.

14. A device for generating a signal dependent upon a liquid film on a surface comprising:
    a temperature changing arrangement for subjecting a portion of the liquid film to a temperature change;
    a temperature measuring arrangement for determining the temperature of the liquid film, the temperature measuring arrangement being capable of producing a signal; and
    a control and evaluation device for controlling one of the temperature changing arrangement and the temperature measuring arrangement,
    wherein the signal produced by the temperature measuring arrangement indicates a thickness of the liquid film.

15. The device of claim 14, wherein the device generates the signal when one of a predetermined thickness and a predetermined thickness range of the liquid film is ascertained.

16. The device of claim 14, wherein the surface is one of a road surface and a traffic surface.

17. The device of claim 14, further comprising an electrode arrangement for identifying the presence of the liquid film in an area of the heating or cooling arrangement.

18. The device of claim 17, wherein the temperature measurement arrangement comprises a measurement device which is connected to the electrode arrangement.

19. The device of claim 14, wherein the temperature changing arrangement comprises at least one Peltier element which is operated at a constant power.

20. The device of claim 14, wherein the temperature changing arrangement comprises one of a heating and a cooling surface which is indented some distance from an exterior surface.

21. The device of claim 20, wherein the liquid is one of heated and cooled in the indented heating and cooling surface.

22. The device of claim 21, wherein the exterior surface is adapted to be aligned with a road surface when the device is disposed in the road surface.

23. A method for generating a signal dependent upon a liquid film on a surface with a device that includes a temperature changing arrangement for subjecting a portion of the liquid film to a temperature change, a temperature measuring arrangement for determining the temperature of the liquid film, the temperature measuring arrangement being capable of producing a signal, and a control and evaluation device for controlling one of the temperature changing arrangement and the temperature measuring arrangement, the method comprising:

subjecting the portion of the liquid film to a temperature change using the temperature changing arrangement;

measuring the temperature of the portion using the temperature measuring arrangement;

assigning the value which corresponds to the thickness of the liquid film to the temperature change using the evaluation device; and producing a signal related to the value.

24. A device for generating a signal dependent upon a liquid film on a surface comprising:

a temperature changing arrangement for subjecting a portion of the liquid film to a temperature change;

a temperature measuring arrangement for determining the temperature of the liquid film, the temperature measuring arrangement being capable of producing a signal;

a control and evaluation device;

a control and evaluation element;

the temperature changing arrangement being coupled to at least one of the control and evaluation device and the control and evaluation element; and the temperature measuring arrangement being coupled to at least one of the control and evaluation device and the control and evaluation element, wherein the signal produced by the temperature measuring arrangement indicates a thickness of the liquid film.

25. A device for generating a signal dependent upon a liquid film on a surface a temperature changing arrangement subjecting a portion of the liquid film to a temperature change;

a temperature measuring arrangement determining the temperature of the liquid film, the temperature measuring arrangement producing a signal; and a control and evaluation device controlling one of the temperature changing arrangement and the temperature measuring arrangement, wherein the signal produced by the temperature measurement arrangement indicates a thickness of the liquid film.

26. A device for generating a signal dependent upon a liquid film on a surface comprising:

a temperature changing arrangement for subjecting a portion of the liquid film to a temperature change;

a temperature measuring arrangement for determining the temperature of the liquid film, the temperature measuring arrangement being capable of producing a signal; and a control and evaluation device for controlling one of the temperature changing arrangement and the temperature measuring arrangement, wherein the temperature measuring arrangement is adapted to measure the temperature of the liquid film at different time intervals, and wherein the control and evaluation device is adapted to evaluate the temperature at the different time intervals and deduce a thickness of the liquid film.

\* \* \* \* \*